United States Patent [19]

Rotman

[11] Patent Number: 4,710,384
[45] Date of Patent: Dec. 1, 1987

[54] SUSTAINED RELEASE TABLETS MADE FROM MICROCAPSULES

[76] Inventor: Avner Rotman, 6 Alkalai Street, Rehovot, Israel

[21] Appl. No.: 889,775

[22] Filed: Jul. 28, 1986

[51] Int. Cl.$^4$ .......................... A61K 9/50; A61K 9/28; A61K 9/26; A61K 9/22
[52] U.S. Cl. .................................... 424/465; 424/468; 424/469; 424/470; 424/489; 424/490
[58] Field of Search ........................ 424/16, 32, 33, 35, 424/21, 465, 468, 469, 470, 489, 490; 514/963

[56] References Cited

U.S. PATENT DOCUMENTS

| | | | |
|---|---|---|---|
| 3,325,365 | 6/1967 | Hotko et al. | 424/489 |
| 3,341,416 | 9/1967 | Anderson | 424/35 |
| 3,400,185 | 9/1968 | Kohnle et al. | 424/35 |
| 3,495,988 | 2/1970 | Balassa | 424/37 |
| 3,860,733 | 1/1975 | Morse et al. | 424/35 |
| 3,911,099 | 10/1975 | De Foney | 424/81 |
| 3,922,338 | 11/1975 | Estevenel et al. | 424/21 |
| 4,016,254 | 4/1977 | Seager | 424/33 |
| 4,113,816 | 9/1978 | Estevenel et al. | 264/113 |
| 4,316,884 | 2/1982 | Alam et al. | 424/19 |

Primary Examiner—Shep K. Rose
Attorney, Agent, or Firm—Browdy and Neimark

[57] ABSTRACT

A tablet for oral adminstration of a sustained-release medication is formed by compressing microcapsules of the active principle. The microcapsules are of a size range between about 5 and 300 microns and comprise particles of active principle coated with a thin, flexible layer of sustained release material. The sustained-release material contains about 15–30% by weight thereof of plasticizer and is coated in an amount corresponding to 10–25% of the weight of the active material. Excipients causing disintegration of the tablet after administration can be uniformly mixed with the microcapsules prior to compression.

6 Claims, 1 Drawing Figure

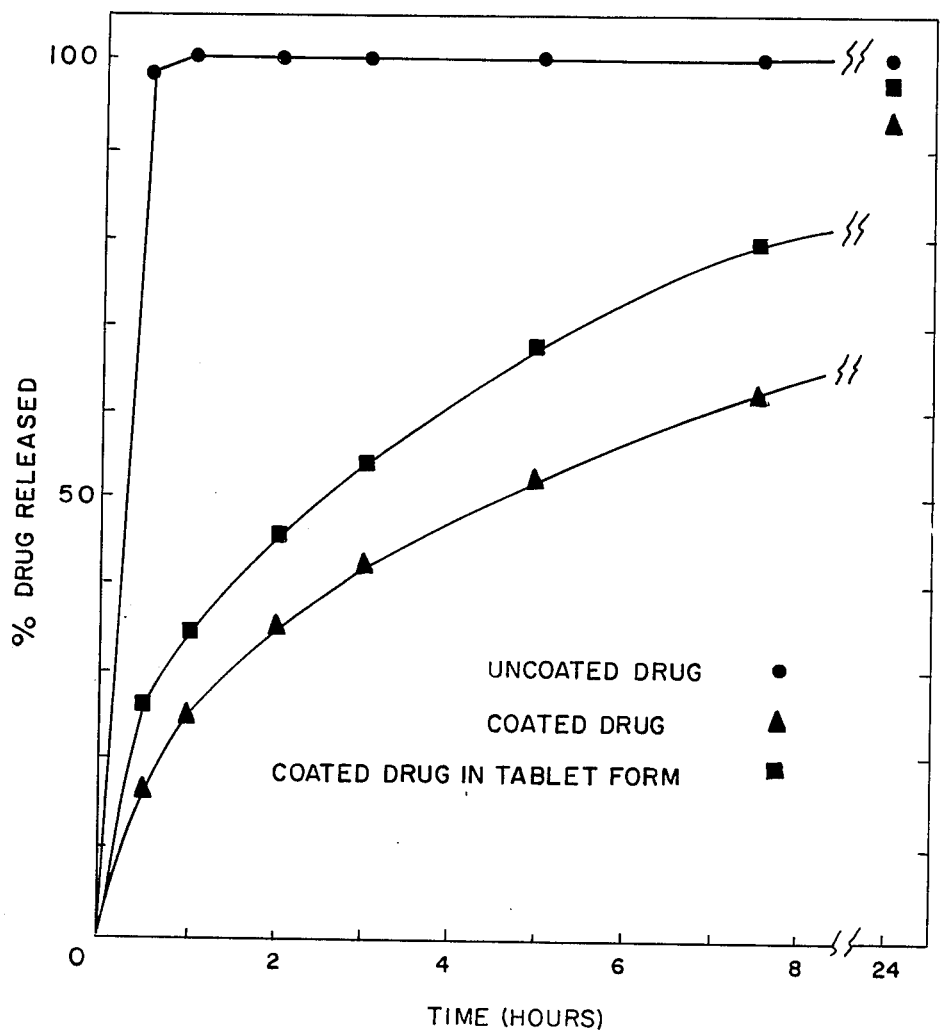

SUSTAINED RELEASE TABLETS MADE FROM MICROCAPSULES

FIELD OF THE INVENTION

The present invention relates to a galenical form of medicament which permits sustained release microcapsules to be formulated into the form of a compressed tablet. The present invention further relates to tablets of sustained release microcapsules which may be in a form for chewable administration.

BACKGROUND OF THE INVENTION

Sustained release medications are well known and are very desirable in order to permit a single dosage of medicament to remain effective over a period of time which may be up to twelve hours or more. Generally, this is accomplished by means of a gelatin capsule holding a plurality of microcapsules of medicament, each capsule being coated with a sustained release coating which permits the medicament to be slowly released through the coating of the microcapsule. Alternatively, the microcapsules may contain a plurality of different coatings so that some of the coatings dissolve almost immediately, some do not dissolve for a number of hours and some are even more stable to prevent release of medicament for many hours.

Gelatin capsules of medicament have fallen into disrepute in recent years as they are subject to tampering. Foreign substances can be placed into such gelatin capsules. Accordingly, administration forms are being sought which will avoid the use of capsules. This is particularly difficult with respect to sustained release medicaments because conventional microcapsules are known to break if subjected to the pressures required to form a tablet. If the microcapsules break, then all of the medicament is released immediately and one has no sustained release effect.

One method by which the prior art has attempted to solve this problem is described in U.S. Pat. Nos. 3,922,338 and 4,113,816. In these patents, controlled release microcapsules are formulated into a tablet by sandwiching the microcapsules between two layers of excipient in granular form which serve to cushion the microcapsules of the medial layer against the shock of compression when compressing them to tablets.

Some prior art tablets achieve sustained release by mixing the drug directly with an excipient which prevents break up of the tablets in the gastric juices or intestinal fluids so that the tablet itself slowly breaks down and releases the active principle over a period of time. For example, formulating the drug with a spongy polymer, such as methyl cellulose, will form a sustained release tablet which gradually releases drug from the polymer. Such galenical forms have the disadvantage, however, of providing high concentrations of active principle at the spot where the tablet rests which in some cases, depending on the medicament, can cause an ulcer or other complications. It is preferred that the tablet break up after administration so as to cause the active principle to disperse and not be too heavily concentrated at one place while still achieving sustained release. No simple and effective way to attain this object has yet been found in the prior art.

SUMMARY OF THE INVENTION

Accordingly, it is an object of the present invention to obviate the problems of the prior art.

It is another object of the present invention to provide a galenical form comprising microcapsules in tablet form.

It is a further object of the present invention to provide chewable tablets composed of microcapsules of sustained release medicament.

It is still a further object of the present invention to provide a sustained release tablet with immediate disintegration into many dispersed centers of sustained drug release.

It is yet a further object of the present invention to provide tablets which permit passage of the active principle immediately into the intestine without the delay of drug release in the stomach.

It is yet a further object of the present invention to provide a sustained release tablet which has a high percentage of active material.

These and other objects of the present invention are accomplished by coating irregular shaped particles of medicament having a range of sizes which is well distributed between about 5 microns and about 300 microns, with a thin flexible layer of coating which usually does not exceed about 20 percent of the weight of the medicament. In order to obtain a sufficiently flexible layer of coating, a relatively high percentage of plasticizer, for example 20 to 25 percent, is used.

When such coated particles of medicament are compressed into a tablet, the wide range of sizes and irregular shapes of the coated particles permit sufficient compression to form a tablet without causing the coating of the medicament particles to break.

Only by using very small particles of medicament, below about 300 microns, and coating with a thin, flexible layer of sustained release material is it possible to compress to a sufficient degree (for example 1.5 tons pressure) to form a tablet without substantial breakage of the microcapsules. Conventional excipients, such as starch or cellulose derivatives, may be thoroughly mixed with the coated particles prior to forming the tablet in order to enhance disintegration of the tablet, after administration, into an individual microcapsules.

BRIEF DESCRIPTION OF THE DRAWING

The drawing is a graph showing the release of drug from microcapsules in tablet form (in vitro) on the basis of percent drug release plotted against time.

DETAILED DESCRIPTION OF PREFERRED EMBODIMENTS

The present invention resides in a particular galenical form of administration of medicament. The particular medicament which is microencapsulated and formed into a tablet in accordance with the present invention may be totally arbitrarily selected. The utility of the present invention does not rely on the particular properties of the material being encapsulated but rather on the particular size of the particles being encapsulated and the type of coating applied. Furthermore, the active principle need not be a pharmaceutical, but may be any material which is desired to be released over a period of time, such as a flavoring substance or an indicator substance.

Those medicaments which are most well suited to the present invention are those which are presently sold in gelatin capsules of encapsulated sustained release drug. These include appetite suppressors, such as phenylpropanolamine, antihistamines such as are present in the commercial product sold under the trademark Contac, sustained release aspirin, sustained release acetaminophen (Tylenol ®), ampicillin, ibuprofen, theophiline and others. This list is only exemplary and the present invention is to be in no way limited by the particular active material present therein.

The particles of active principle should be chosen with a size which will permit all of the coated particles to be below about 300 microns in diameter, preferably between 30 and 250 microns. Furthermore, the size should be selected to be well distributed within the entire size range. By using a wide range of different sizes of particles, which particles are essentially crystals of irregular shape and which shape remains irregular after coating because of the thin nature of the coating, the coated powder becomes well packed during compression thereby minimizing breakage.

The specific nature of the coating material is not critical in accordance with the present invention as long as sufficient plasticizer is present to permit the required degree of flexibility of the coating. Thus, any conventional sustained release coating, such as the coatings sold under the trademark Eudragit RS or RL, may be used, as can ethyl cellulose and other known sustained release coatings. The present invention is not to be limited to the particular coating used on the particles of active principle.

It is important that a relatively high percentage of plasticizer be used in the coating in order to permit sufficient flexibility to prevent substantial breakage during compression. The specific amount of plasticizer will, of course, vary depending on the nature of the coating and the particular plasticizer used. The amount may be readily determined empirically by testing the release characteristics of the tablets formed. If the medicament is being released too quickly, then more plasticizer should be used. On the other hand release characteristics are also a function of the thickness of the coating. When substantial amounts of plasticizer are used, the sustained released capacity of the coating diminishes. Thus, the thickness of the coating may be increased slightly to make up for an increase in the amount of plasticizer. It should seldom be necessary, however, to use an amount of coating which exceeds about 20 percent of the total weight of the final product. Generally, the plasticizer will be present in an amount of about 15 to 30 percent of the sustained release material in the coating, preferably 20 to 25 percent and the amount of coating will be from 10 to 25 percent of the weight of active material, preferably 15 to 20 percent.

Any conventional pharmaceutically acceptable plasticizer may be used. While castor oil is exemplified herein, the present invention is not limited thereto and other conventional plasticizers may be used for their known film plasticizing properties.

The coating may be applied to the powder by techniques known per se in the prior art. The present invention does not reside in the particular technique of coating. The preferred method of coating the particles is by a fluidized bed technique using, for example, a Uni-Glatt fluidized bed powder coating apparatus.

The coated particles may be compressed into tablets directly or with the addition of conventional binders, fillers, diluents, excipients, flavoring agents, lubricants, etc. Any such pharmaceutically acceptable material may be present although it is preferred that excipients be avoided which prevent disintegration of the tablets, after administration, into their constituent coated particles. On the contrary, it may be preferred to use an excipient which causes prompt disintegration of the tablets, after administration into many disperse centers of drug release. Known excipients which may be used for such purposes include starch and microcrystalline cellulose. Other known excipients and carriers useful for this purpose may also be used.

The excipients and flavorings, binders, fillers, etc., are preferably thoroughly mixed with the coated particles prior to tableting. It is not necessary or desirable to sandwich the particles between layers of excipient.

When the material is ready to be compressed into tablets, it may be formed into tablets by any conventional tableting apparatus. The thin flexible coatings on ultra small particles of a wide range of sizes, all below 300 microns, permit compression and packing into a tablet at all conventional tableting pressures without substantial breakage of the microcapsules.

A particular advantage of the use of microcapsules below about 300 microns is that they may be administered in the form of a chewable tablet. Because of the very small size of the capsules, it has been discovered that very few capsules are actually broken during the act of mastication of the tablet. Thus, for the first time it is possible to administer a sustained release medicine in the form of a chewable tablet. Most conventional coated particles in commercial encapsulated microcapsules have a size range between 600 and 1000 microns. If these are chewed, there will be substantial breakage causing immediate release of what may be an overdose of medication and what is usually a very distinctive and unpleasant medicament taste. When using particles below about 300 microns, the taste of the medicament may be thoroughly masked, even upon chewing, because the particles are small enough to pass into the curves and depressions of the teeth and thus avoid substantial breakage.

Another unexpected advantage of microcapsules below about 300 microns each is the fact that they pass through the stomach without delay in the stomach. Because of their small size the coated drug particles are transferred immediately into the intestines with the speed of a liquid. They need not even be enteric coated as the vast majority will quickly pass directly into the intestine without releasing the active principle in the stomach. Larger conventional size microcapsules remain for a much longer period in the stomach, thus preventing quick release of the medicament in the intestines. Using small particles allows the active principle to reach the blood stream much faster.

The following examples are provided for ease of illustration only and is not intended to be limiting in any way.

EXAMPLE 1

One kg of acetaminophen (paracetamol) was coated in a modified Uni-Glatt powder coater with ethyl cellulose. The acetaminophen had a crystal size of 74–500 microns. The ethyl cellulose used was type 10 ethyl cellulose obtained from Dow Chemical Company. The spraying solution comprised an 8 percent solution of the ethyl cellulose in 90 percent acetone-10 percent ethanol. To this was added castor oil as plasticizer in an amount equal to 20 percent of the ethyl cellulose present.

The spraying conditions were as follows:

(i) Speed: 1 liter/hour
(ii) Flap: 10–15 percent
(iii) Inlet Temperature: 50° C.
(iv) Outlet temp.: 30° C.
(v) Percent of Coating: 17 percent The coated acetaminophen was sieved to particle sizes between 74–210 microns. Attention was paid to ensure a good mix of particles of different sizes within that range. 400 mg of the coated particles were mixed with 100 mg of starch and the mixture was compressed in a hand press to 1.5 tons to produce 500 mg tablets.

EXPERIMENT 1

The release characteristics of the tablets obtained in example 1 were tested by placing a tablet in 50 ml of simulated intestinal fluid. The tablet disintegrated within 5 to 10 seconds into many microcapsules. Similar disintegration was observed when such a tablet was added to simulated gastric fluid.

The release pattern of acetaminophen, in vitro in simulated intestinal fluid was measured. The results are shown in the drawing. The uncoated drug showed 100 percent release of the drug within a very short period of time. Coated drug, but not tableted, showed that release of the drug continued for about 24 hours with half of the drug being released in approximately 10 hours. After compression of the drug was released for a total of about 16 hours with half of the drug being released after about 5 hours.

While release of the drug is slightly faster in the tableted form, a relatively small percent is immediately released, thus showing that relatively few microcapsules were broken during compression.

Tests with tablets formed from commercial size coated particles of 600–1000 microns (see Experiment 2) showed that the pellets were completely broken by the compression and the release characteristics were substantiall identical to the line on the graph for uncoated drug.

Accordingly, within the parameters of the present invention, as discussed hereinabove, the coating can be adjusted to provide the desired release characteristics in the compressed tablet.

EXPERIMENT 2

Commercial microcapsules were sampled to evaluate their size. They were sized with a regular dual-purpose laboratory sieve shaker (Ari J. Levi Ltd). The results were as follow:
1. Theotard (CTS, Israel ): 100% over 800$\mu$
2. Dexatrim (Thompson Med., N.Y.): 95% over 800$\mu$; 5% between 600–800$\mu$
3. Theo-24 (Searle): 100% over 800$\mu$
4. Eryc 250 mg (Parke-Davis): 100% over 800$\mu$
5. Feosol (Menley & James): 100% over 800$\mu$
6. Sudafed (Burroughs Wellcome): 100% over 800$\mu$
7. Nitroglycerin (Ascot): 100% over 800$\mu$
8. Thorazine (SKF): 100% over 800$\mu$
9. Slo-phylline (Rorer): 100% over 800$\mu$
10. Nicobid (Armour): 100% over 800$\mu$
11. Teldrin (SKF): 30% over 800$\mu$; 70% between 600–800$\mu$
12. Pavabid (Marion): 100% over 800$\mu$
13. Ornatos (Rohm Pharma, Germany): 60% over 800$\mu$; 40% between 600–800$\mu$
14. Somophylline (Fisons): 97% over 800$\mu$; 3% between 600–800$\mu$
15. Contac (Menley & James): 33–40% over 800$\mu$; 60–67% between 600–800$\mu$

EXAMPLE 2

An acrylic resin coating polymer may be prepared by dissolving 170 gms Eudragit RS-100 (Rohm Pharma, Germany) dissolved in isopropyl alcohol (60%) and acetone (40%). Eudragit RS-100 is a sustained release acrylic resin preparation which is poorly permeable. The final polymer concentration was 8%. To this solution is added 0.5 gms of pigment (Blue Lake ZLT 2), 17 gms talc, and 8.5 gms magnesium stearate and 34 gms castor oil as plasticizer.

One kg theophylline, crystal size between 44–800$\mu$, is coated with the acrylic resin polymer using a modified Glatt fluidized bed coating instrument (UniGlatt). The theophylline powder is fluidized and coated with the polymer. Technical details of the coating process are:
Air Flap: 25%
Inlet air temp.: 50° C.
Outlet (product) temp.: 35° C.
Spraying air pressure: 1.5 bar
Pneumatic pressure: 6 bars
Polymer solution feeding speed: 400 ml/n
Process time: 5.5 hrs The coated powder is sieved with a regular dual-purpose laboratory sieve shaker (Ari J. Levi Ltd.) and different fractions collected.

The obtained microcapsules in the 50–250$\mu$ range may be compressed into tablets in the same manner described with respect to Example 1.

EXPERIMENT 3

A test was conducted to measure the release of theophylline from various sized microcapsules using an artificial mouth. The artificial mouth used in this test was a plastic artificial mouth model manufactured by Frasaco having upper and lower jaws with teeth of natural size and configuration.

Two batches each of ten mg of coated particles were prepared as described in Example 2 but without the addition of plasticizers. One batch had a size range of 100–150$\mu$ and 600–800$\mu$. Each contained a total of 8.3 mg theophylline. The coated particles were placed on the bottom rear teeth of the model. The model was closed and pressure was applied on the top corresponding to 2 kg for 10 sec. Then a twisting of the two rows of teeth was performed for another 15 sec. The particles (or their remains) were transferred to a test tube and the teeth were washed with 2 ml of water which was collected and transferred into the tube. The test tubes were centrifuged in a clinical centrifuge for 3 min. and the supernatant was removed. The amount of theophylline in each tube was determined by u.v. spectroscopy with the following results:
  I. Large crystals (600–800$\mu$): 2.04 mg theophylline released into the medium (24.5%)
  II. Small crystals (100–150$\mu$): 24 $\mu$g theophylline were released into the medium (0.29%)

In a control experiment it was shown that the release, due to diffusion, of theophylline through 17% coating layer of Eudragit RS-100 is less than 1% during a 5 min. period. Thus, the amount of uncoated theophylline found in the large crystals sample is due to breaking of the coated crystals by the mechanical pressure and friction of the teeth. Such a substantial release using large microcapsules is unacceptable for a sustained release dosage form. Results at least as good would be expected if the smaller microcapsules were made even more flexible by adding plasticizer.

The results of this test provide further evidence of the superior results obtainable using the preferred microcapsule size when preparing a dosage form designed to be ingested with mastication as compared to the use of microcapsules of the commercial size, particularly when the coating is a sustained release coating.

Experiments similar to that of Example 1 and Experiment 1 were conducted with theophylline, phenylpropanolamine and ibuproten and similar results were obtained.

The embodiments of the invention described above are given by way of example only as constituting forms of the invention within the general scope thereof as defined broadly in the succeeding claims.

What is claimed is:

1. A new sustained release galenical form in the form of a disintegratable tablet, comprising compressed microcapsules of active principle and a pharmaceutically acceptable excipient interspersed among and throughly mixed with said microcapsules, wherein said microcapsules have a size range distributed between about 5 and about 300 microns and comprise particles of active principle coated with an encapsulating layer of an ethyl cellulose or acrylic resin sustained release polymer containing a sufficient amount of plasticizer to render said coating flexible, said amount being within the range of about 15 to about 30% of the weight of said sustained release polymer, said coating being no thicker than that which forms 25% of the weight of the active principle.

2. A galenical form in accordance with claim 1, wherein said excipient includes a material for causing disintegration of the tablet after administration.

3. A galenical form in accordance with claim 1, wherein said plasticizer is present in an amount of about 15-20% of the weight of said sustained release polymer.

4. A galenical form in accordance with claim 1, wherein said microcapsules have a size range distributed between about 30 and about 250 microns.

5. A galenical form in accordance with claim 1, wherein said sustained release polymer is coated on said active principle in an amount corresponding to 10-25% of the weight of the active material.

6. A galenical form in accordance with claim 5, wherein said sustained release polymer is coated on said active principle in an amount corresponding to 15-20% of said active material.

* * * * *